United States Patent

Galey et al.

[11] Patent Number: 6,007,827
[45] Date of Patent: *Dec. 28, 1999

[54] METHOD OF DEPIGMENTING OR BLEACHING MAMMALIAN SKIN USING L-2-OXOTHIAZOLIDINE-4-CARBOXYLIC ACID

[75] Inventors: Jean-Baptiste Galey, Aulnay-Sous-Bois; Laurent Marrot, Livry Gargan; Catherine Causse, Paris; Rainer Schmidt, Paris; Marcelle Regnier, Paris, all of France

[73] Assignee: L'Oreal, Paris, France

[*] Notice: This patent issued on a continued prosecution application filed under 37 CFR 1.53(d), and is subject to the twenty year patent term provisions of 35 U.S.C. 154(a)(2).

[21] Appl. No.: 08/773,514

[22] Filed: Dec. 23, 1996

[30] Foreign Application Priority Data

Dec. 22, 1995 [FR] France .................... 95 15335

[51] Int. Cl.⁶ .............. A61K 6/00; A61K 7/00; A61K 7/04
[52] U.S. Cl. ............................. 424/401; 424/62
[58] Field of Search ................................ 424/62

[56] References Cited

U.S. PATENT DOCUMENTS

| | | |
|---|---|---|
| 4,335,210 | 6/1982 | Meister et al. . |
| 4,434,158 | 2/1984 | Meister et al. . |
| 4,438,124 | 3/1984 | Meister et al. . |
| 4,647,571 | 3/1987 | Meister et al. . |
| 4,665,082 | 5/1987 | Meister et al. . |
| 4,879,370 | 11/1989 | Meister .................... 530/331 |
| 4,990,330 | 2/1991 | Oyama ..................... 424/59 |
| 5,208,249 | 5/1993 | Rowe et al. ............. 514/367 |
| 5,262,153 | 11/1993 | Mishima et al. ........... 424/62 |
| 5,331,091 | 7/1994 | Fukuda et al. ........... 530/350 |
| 5,407,667 | 4/1995 | Matuura et al. ........... 424/62 |
| 5,624,955 | 4/1997 | Nagasawa et al. ........ 514/513 |

FOREIGN PATENT DOCUMENTS

| | | |
|---|---|---|
| 0 117 176 | 8/1984 | European Pat. Off. . |
| 0 650 725 A1 | 5/1995 | European Pat. Off. . |
| 0 656 201 A1 | 6/1995 | European Pat. Off. . |

*Primary Examiner*—Thurman K. Page
*Assistant Examiner*—Sharon Howard
*Attorney, Agent, or Firm*—Oblon, Spivak, McClelland, Maier & Neustadt, P.C.

[57] ABSTRACT

A cosmetic composition for depigmenting or bleaching mammalian skin or both, which contains:

a) an amount of L-2-oxothiazolidine-4-carboxylic acid effective to depigment or bleach mammalian skin or both, and b) a topically-acceptable carrier.

9 Claims, No Drawings

METHOD OF DEPIGMENTING OR BLEACHING MAMMALIAN SKIN USING L-2-OXOTHIAZOLIDINE-4-CARBOXYLIC ACID

BACKGROUND OF THE INVENTION

1. Field of the Invention

The present invention relates to the use of L-2-oxothiazolidine-4-carboxylic acid as a depigmenting or bleaching agent in a cosmetic and/or dermatological composition.

DESCRIPTION OF THE BACKGROUND

The color of mammalian, such as human, skin depends on many factors and, in particular, on the seasons of the year, race and sex, for example. It is, however, mainly determined by the concentration of melanin produced by melanocytes.

However, it has been sought for several years to reduce and/or slow down production of melanin in order to depigment or bleach the skin, by acting on one or more of the intermediates in the intracellular biochemical synthesis of melanin. In fact, for many years, different chemical entities have been tested and used as depigmenting or bleaching agents.

In particular, compounds such as vitamin C, vitamin C derivatives or vitamin E derivatives, arbutin, hydroquinone, kojic acid, placenta derivatives and glutathione and derivatives thereof have already been incorporated into compositions.

The above compounds are known to act on the synthesis and/or activity of tyrosinase, an enzyme which plays a part in the synthesis of melanin, or are known to reduce the amount of melanin formed or, alternatively, are known to stimulate the removal of melanin via keratinocytes. Unfortunately, these compounds are either toxic when applied to the skin, in the case of hydroquinone, are unstable in solution, in the case of vitamin C and kojic acid, which complicates the manufacture of the composition, or have unpleasant odors, in particular, sulphurous odors, such as glutathione, which consequently limits the use thereof. Moreover, the above tyrosinase- or tyrosinase synthesis-inhibitors are very limited in number.

Thus, a need exists for a skin bleaching agent which is as effective in its action as those that are known but which avoids the above drawbacks, i.e. one which is stable in a composition, which is not toxic to the skin and which has no unpleasant odors, particularly upon application.

SUMMARY OF THE INVENTION

Accordingly, it is an object of the present invention to provide a skin depigmenting or bleaching agent which is non-toxic and has no unpleasant odors.

It is, moreover, an object of the present invention to provide a method for depigmenting or bleaching skin.

The above objects and others are provided by a composition for depigmenting or bleaching mammalian skin or both, which contains an effective amount of L-2-oxothiazolidine-4-carboxylic acid and a topically acceptable carrier.

DETAILED DESCRIPTION OF THE PREFERRED EMBODIMENTS

The present invention is predicated upon the surprising discovery that L-2-oxothiazolidine-4-carboxylic acid may be used, quite effectively, to depigment or bleach mammalian skin. This is, indeed, surprising since, conventionally, L-2-oxothiazolidine-4-carboxylic acid has been used as a hair loss inhibitor as in EP 0 656 201 A1.

The present invention, thus, provides L-2-oxothiazolidine-4-carboxylic acid in a cosmetic composition as a depigmenting and/or bleaching agent.

The present invention also provides a method for the preparation of a dermatological composition for depigmenting and/or bleaching of mammalian, particularly human, skin.

On contact with the skin, L-2-oxothiazolidine-4-carboxylic acid affords the advantage of not generating an unpleasant release of sulphurous odor.

In accordance with the present invention, L-2-oxothiazolidine-4-carboxylic acid may be present in the present composition in an amount ranging from about 0.1 to 10% by weight and preferably from about 2 to 5% by weight relative to the total weight of the composition. Moveover, the amount of the composition applied on the skin may vary and depends upon the user. Thus, for example, if 10 g of composition were applied, from about 0.01 g to 1 g of L-2-oxothiazolidine-4-carboxylic acid would be administered. However, amounts of more or less than this amount may be used as desired. Generally, the more compound used, the greater the bleaching effect obtained.

The composition according to the present invention may further contain any one or more ingredients conventionally used in the cosmetic or dermatological field, in standard or conventional concentrations. These ingredients may, for example, be fatty substances, preserving agents, vitamins, gelling agents, fragrances, surfactants, water, antioxidants, fillers, moisturizers or screening agents, or mixtures thereof.

Among the fatty substances which may be used are a mineral or synthetic oil, a wax, a silicone, a fatty alcohol or a fatty acid. The oil may be liquid petrolatum or jojoba oil, and the wax may be sipol wax, for example. These oils and these waxes may be of either natural or synthetic origin.

The surfactants may be sodium mono diglyceryl stearate or sodium stearate, for example, and the gelling agents may be polyethylene glycols, which are optionally oxyethylenated.

The composition of the present invention may be in the form of an aqueous, aqueous-alcoholic or oily solution, an oil-in-water or water-in-oil emulsion, an aqueous or oily gel, or a dispersion of vesicles, in particular lipid vesicles, for example. This composition may be relatively fluid and have the appearance of a cream, an ointment, a milk, a lotion, a paste or a foam, for example. This composition may optionally be applied to the skin in aerosol form.

The present invention also relates to a cosmetic and/or dermatological process for depigmenting and/or bleaching mammalian skin, which entails applying to the skin of a mammal in need thereof an effective amount of L-2-oxothiazolidine-4-carboxylic acid, preferably in a composition containing the same.

The present invention will now be further illustrated by several examples which follow, in which concentrations are given as percentage by weight. These examples are provided solely for purposes of illustration and are not intended to be limitative.

| Example 1: Bleaching cream for the face | |
|---|---|
| L-2-Oxbthiazolidine-4-carboxylic acid | 2 |
| Sodium stearate | 3 |
| Liquid petrolatum | 6 |
| Alkyl paraben | 0.05 |
| Potassium sorbate | 10 |
| Stearyl alcohol | 1 |
| Fragrance | 1 |
| Water | 100 |

| Example 2: Bleaching cream for the body | |
|---|---|
| L-2-Oxothiazolidine-4-carboxylic acid | 5 |
| Jojoba oil | 13 |
| Sipol wax | 6 |
| Isopropyl palmitate | 2 |
| Glycerol | 15 |
| Alkyl paraben | 0.5 |
| Fragrance | 1 |
| Water | 100 |

Having described the present invention, it will be apparent to the artisan that many changes and modifications may be made to the above-described embodiments without departing from the spirit and the scope of the present invention.

What is claimed as new and desired to be secured by Letters Patent of the United States is:

1. A method of depigmenting or bleaching mammalian skin, which comprises administering to the skin of a mammal a depigmenting or bleaching effective amount of L-2-oxothiazolidine-4-carboxylic acid.

2. The method of claim 1, wherein said L-2-oxothiazolidine-4-carboxylic acid is in a cosmetic composition containing from about 0.1 to 10% by weight based upon the total weight of the composition.

3. The method of claim 1, wherein said mammal is a human.

4. The method of claim 2, wherein said L-2-oxothiazolidine-4-carboxylic acid is present in an amount of from about 2 to 5% by weight.

5. The method of claim 2, wherein said composition is topically administered.

6. The method of claim 2, wherein said composition is aerosolically administered.

7. The method of claim 2, wherein said composition is in a form of an aqueous solution, aqueous-alcoholic solution, oily solution, oil-in-water emulsion, water-in-oil emulsion, aqueous gel, oily gel or vesicle dispersion.

8. The method of claim 2, wherein said composition further comprises one or more of fatty substances, preserving agents, vitamins, gelling agents, fragrances, surfactants, water, antioxidants, fillers, moisturizers or screening agents.

9. The method of claim 8, wherein said fatty substance comprises an oil, wax, silicone, fatty alcohol or fatty acid.

* * * * *